United States Patent [19]
Hosoi

[11] Patent Number: 6,120,149
[45] Date of Patent: Sep. 19, 2000

[54] EYE REFRACTIVE POWER MEASUREMENT APPARATUS

[75] Inventor: Yoshinobu Hosoi, Gamagori, Japan

[73] Assignee: Nidek Co., Ltd., Japan

[*] Notice: This patent is subject to a terminal disclaimer.

[21] Appl. No.: 09/181,876

[22] Filed: Oct. 29, 1998

[30] Foreign Application Priority Data

Oct. 31, 1997 [JP] Japan .................................... 9-316152

[51] Int. Cl.$^7$ ...................................................... A61B 3/10
[52] U.S. Cl. .............................................................. 351/205
[58] Field of Search ................................... 351/204, 205, 351/206, 211, 212, 246, 247

[56] References Cited

U.S. PATENT DOCUMENTS

| | | | |
|---|---|---|---|
| 5,406,076 | 4/1995 | Mimura et al. ......................... | 250/229 |
| 5,500,697 | 3/1996 | Fujieda ................................... | 351/212 |
| 5,777,718 | 7/1998 | Kohayakawa ........................... | 351/211 |
| 5,805,268 | 9/1998 | Hosoi et al. ............................. | 351/211 |
| 5,892,567 | 3/1999 | Hosoi et al. ............................. | 351/211 |

*Primary Examiner*—George Manuel
*Attorney, Agent, or Firm*—Finnegan, Henderson, Farabow, Garrett & Dunner, L.L.P.

[57] ABSTRACT

An eye refractive power measurement apparatus including measurement device for objectively measuring a refractive power of an eye to be examined, the apparatus comprising memory device for storing a plurality of measurement results obtained by the measurement device, typical value determination device for determining a typical value of the measurement results based on the plurality of the measurement results stored in the memory device, judging device for judging whether or not the eye possibly has low hyperopia based on the plurality of the measurement results stored in the memory device, recommendation value determination device for determining a recommendation value which is different from the typical value if the judging device judges that the eye possibly has low hyperopia and data output device for outputting data indicating the typical value and/or the recommendation value.

20 Claims, 4 Drawing Sheets

EYE REFRACTIVE POWER MEASUREMENT APPARATUS

BACKGROUND OF THE INVENTION

1. Field of the Invention

The present invention relates to an eye refractive power measurement apparatus which objectively measures a refractive power of an eye to be examined.

2. Description of Related Art

It is conventionally known an eye refractive power measurement apparatus which projects a target for measurement onto a fundus of an eye to be examined and objectively measures a refractive power of the eye based on the reflected light therefrom. When precisely measuring a refractive power of the eye using this kind of apparatus, the measurement is carried out usually by relaxing accommodation of the eye by a fogging mechanism and the measurement is repeated a plurality of times. Statistical processes are given to the measurement results obtained thereby such as letting the median or the average be the typical value of the all data values indicating the eye refractive power. The value obtained through the statistical processes is utilized as an initial value in a subjective measurement to be performed next.

However, when measuring an eye which has low hyperopia, an examinee looks into the apparatus and thus so-called instrumental myopia is often caused. As a result, the accommodation of the eye is likely to be unstable. Owing to the unstableness of the accommodation, it may be the case where all the measurement results indicate a negative (or minus) spherical power, or only one result out of three indicates a positive (or plus) spherical power. Upon these cases, if decided in the aforementioned way, the typical value will be of a negative power. Judging from this typical value, an examiner may diagnose that the eye as myopia. If a subjective refractive power measurement is started from a negative spherical power, with a continues accommodation, it is extremely difficult to obtain corrective spherical value for the hyperopic eye by relaxing the accommodation.

SUMMARY OF THE INVENTION

The present invention has been made in view of the above circumstances and has an object to overcome the above problems and to provide an eye refractive power measurement apparatus capable of providing a measurement result which secures accuracy in a subjective refractive power measurement to be performed next even in cases measuring an eye which possibly has low hyperopia.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an eye refractive power measurement apparatus including measurement means for objectively measuring a refractive power of an eye to be examined, the apparatus comprises memory means for storing a plurality of measurement results obtained by the measurement means, typical value determination means for determining a typical value of the measurement results based on the plurality of the measurement results stored in the memory means, judging means for judging whether or not the eye possibly has low hyperopia based on the plurality of the measurement results stored in the memory means, recommendation value determination means for determining a recommendation value which is different from the typical value if the judging means judges that the eye possibly has low hyperopia and data output means for outputting data indicating the typical value and/or the recommendation value.

In another aspect of the present invention, an eye refractive power measurement apparatus including measurement means for objectively measuring a refractive power of an eye to be examined, the apparatus comprises memory means for storing a plurality of measurement results obtained by the measurement means, typical value determination means for determining a typical value of the measurement results by giving a predetermined statistical process to the plurality of the measurement results stored in the memory means, judging means for judging that the eye possibly has low hyperopia if both positive and negative spherical powers are included in the plurality of measurement results stored in the memory means, all of the measurement results includes 0 diopter spherical power, both 0 diopter and negative spherical powers are included in the plurality of the measurement results, or all of the measurement results includes negative spherical powers and are greater than a predetermined negative spherical power, recommendation value determination means for determining a recommendation value which is different from the typical value by giving a predetermined process if the judging means judges that the eye possibly has low hyperopia and data output means for outputting data indicating the typical value and/or the recommendation value.

In another aspect of the present invention, an eye refractive power measurement apparatus for measuring a refractive power of an eye to be examined, the apparatus comprises objective measurement means for objectively measuring the refractive power of the eye, memory means for storing a plurality of measurement results obtained by the objective measurement means, typical value determination means for determining a typical value of the measurement results based on the plurality of the measurement results stored in the memory means, judging means for judging whether or not the eye possibly has low hyperopia based on the plurality of the measurement results stored in the memory means, recommendation value determination means for determining a recommendation value which is different from the typical value if the judging means judges that the eye possibly has low hyperopia, subjective measurement means for subjectively measuring a refractive power of the eye and subjective measurement control means for controlling the subjective measurement means based on data indicating the typical value and/or the recommendation value.

According to the present invention, even in cases of measuring an eye which possibly has low hyperopia, the apparatus is capable of providing measurement data which helps a subjective refractive power measurement which is performed next to be accurate.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
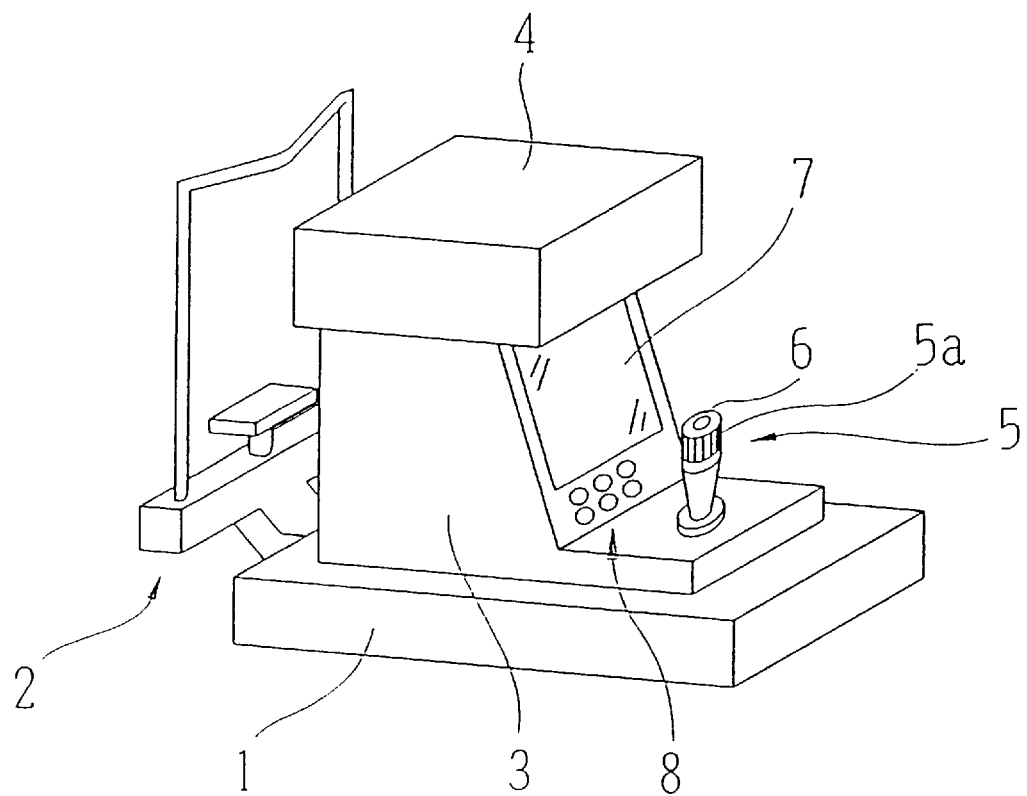
FIG. 1 is an overview of an eye refractive power measurement apparatus of the preferred embodiment of the present invention.

A detailed description of one preferred embodiment of an objective eye refractive power measurement apparatus embodying the present invention will now be given referring to the accompanying drawings. FIG. 1 is an overview of the apparatus of the preferred embodiment of the present invention. Reference numeral 1 denotes a base and 2 is a face support unit for supporting an examinee's face. 3 is a body and 4 is a measuring part containing optical systems as hereinafter described. Responding to operations of a joystick 5, the body 3 slides along a horizontal plane of the base 1 in back-and-forth and side-to-side directions. By turning a rotation knob 5a, the measuring part 4 moves in up-and-down directions in relation to the body 3. For the details of this joystick mechanism, see U.S. Pat. No. 5,406,076 which corresponds to Japanese Patent Publication of unexamined patent application No. HEI 6-7292 by the present applicant. The joystick 5 is provided with a measurement starting switch 6 at the top thereof. 7 is a TV monitor to display information such as an image of an anterior part of the eye and the like. 8 is a switch part which includes a print switch, a setting switch utilized upon output of a reference value for low hyperopia and the like.

Figure 2:
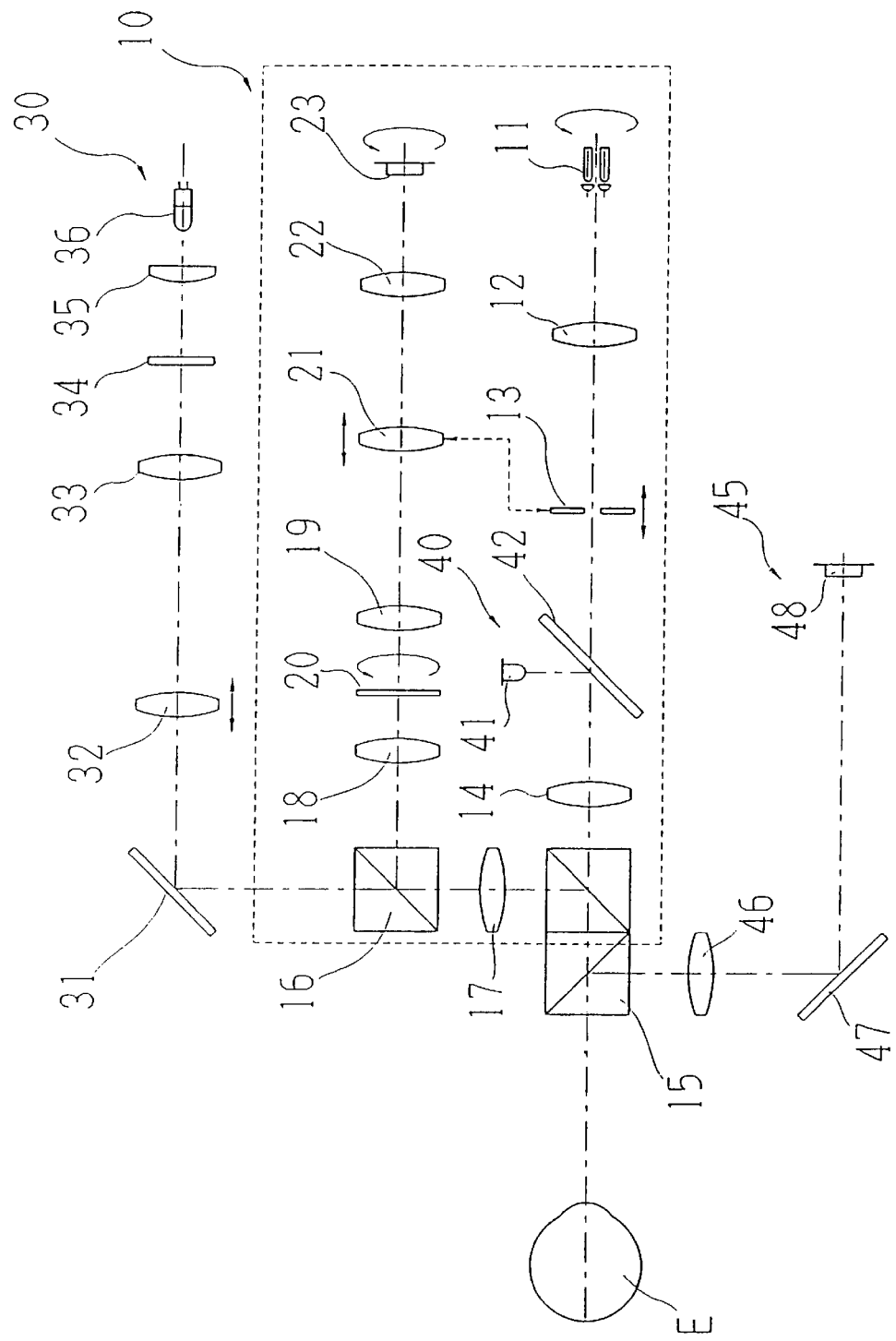
FIG. 2 is a view showing a schematic arrangement of optical systems of the apparatus.

FIG. 2 is a view showing a schematic arrangement of the optical systems of the apparatus. Reference numeral 10 denotes an eye refractive power optical system. 11 is a pair of light sources for measurement which emits measurement light having its wavelength within an infrared range. The light sources 11 are arranged to be rotatable on an optical axis. 12 is a condenser lens. 13 is a target plate for measurement provided with a target for measurement (a spot aperture) thereon. The target plate 13 is movable so as to be moved to a conjugate position with a fundus of the eye E. 14 is a projecting lens, 15 and 16 are beam splitters, 17 is an objective lens, 18 and 19 are relay lenses. 20 is a strip-shaped corneal reflection eliminating mask which is arranged at a conjugate position with a cornea of the eye E to be rotatable on an optical axis. 21 is a movable lens which moves along with the target plate 13. 22 is an image forming lens. 23 is a photo-detector for measurement which rotates about the optical axis being synchronized with the light sources 11 and the corneal reflection eliminating mask 20.

Reference numeral 30 denotes a fixation target optical system. 31 is a mirror. 32 is a first relay lens which moves along an optical axis and thereby fogs the eye E. 33 is a second relay lens, 34 is a fixation target which is arranged at a focal point of the second relay lens 33. 35 is a condenser lens and 36 is an illumination lump.

Reference numeral 40 denotes a target projecting optical system which projects a light bundle to form an image of a target for alignment from a direction of a visual axis. A point light source 41 emits infrared light for projecting a target. The light from the light source 41 is first reflected by a beam splitter 42 and then passes through the projecting lens 14 thereby made to be parallel to the visual line. The light will be projected from the front of the eye E along the optical axis for measurement so that an image of the target for alignment is formed upon the cornea.

Reference numeral 45 denotes an observation target detection optical system. An image of an anterior part of the eye E illuminated by unillustrated light source and the image of the target for alignment formed by the target projecting optical system 40 are first reflected by the beam splitter 15, and then photographed by a CCD camera 48 through an object lens 46 and a mirror 47. It is also possible to separately provide an observation optical system and a target detection optical system to detect the target image for alignment which is projected onto the eye E.

Figure 3:
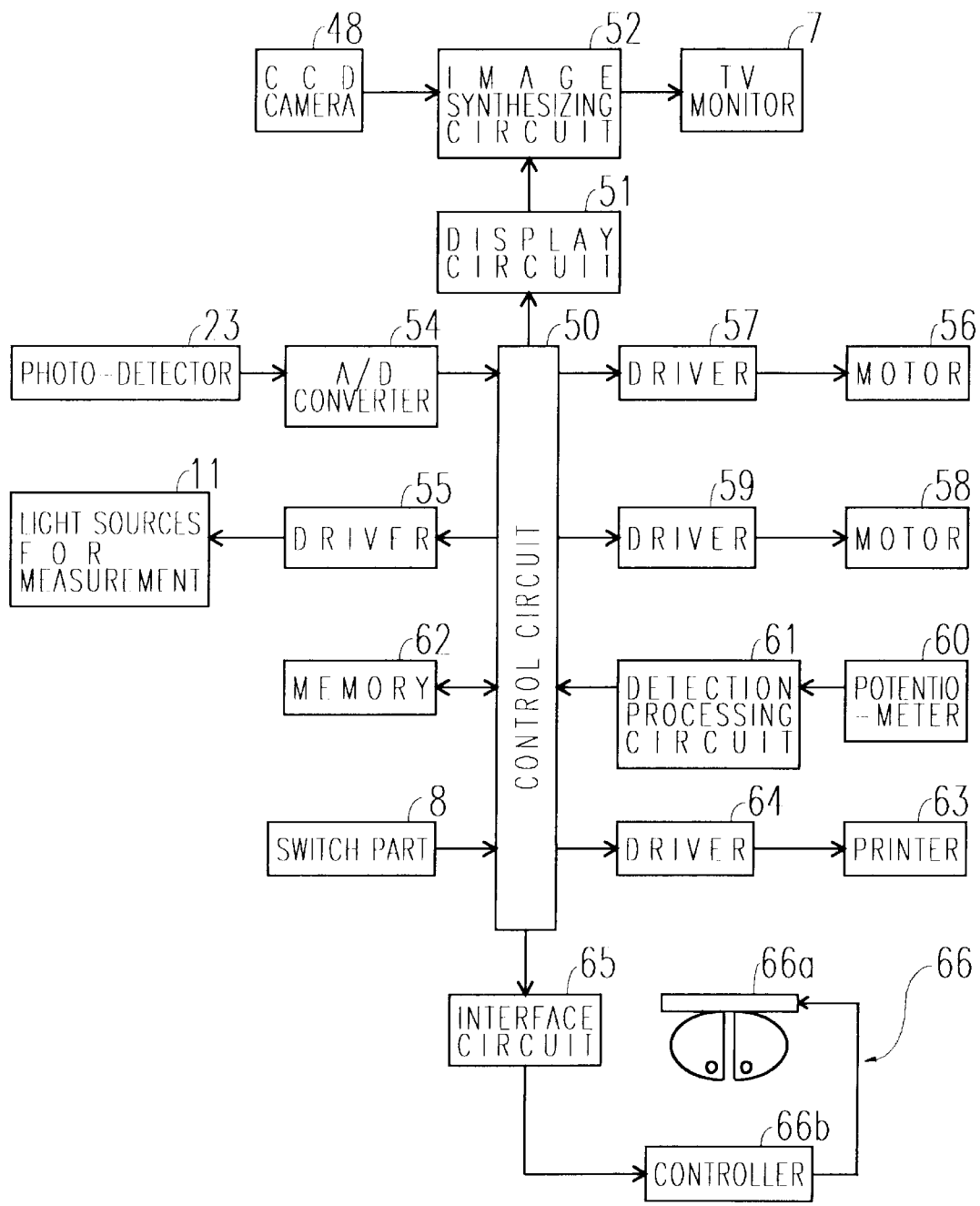
FIG. 3 is a view showing a schematic arrangement of a control system of the apparatus.

FIG. 3 is a view showing a schematic arrangement of a control system of the apparatus. Picture signals from the CCD camera 48 are synthesized in an image synthesizing circuit 52 with signals of characters and graphics which are generated in a display circuit 51 so as to be displayed on the TV monitor 7. A control circuit 50 for controlling the whole apparatus is connected to an A/D converter 54 which digitizes signals from the photo-detector 23, a driver 55 for the light sources 11, a driver 57 for a motor 56 which rotates the light sources 11, the corneal reflection eliminating mask 20 and the photo-detector 23, a driver 59 for a motor 58 which moves the target plate 13 and the movable lens 21, and the like (although it is not illustrated, each of the divers for the first relay lens 32, the illumination lump 36 and the point light source 41 is likewise connected to the controller 50). 60 is a potentiometer which detects a position of the target plate 13 (the movable lens 21) and 61 is a detection processing circuit for the detection. 62 is a memory to store the measurement result. 63 is a printer and 64 is a driver for the printer 63. An interface circuit 65 is connected to a subjective refractive power measurement apparatus 66 and sends/receives data therebetween. The subjective refractive power measurement apparatus 66 is the type of apparatus which is provided with a lens unit 66a; the lens unit 66a which is composed of a pair of right and left parts places one optical element among various kinds of optical elements alternatively at a test window by electric power. 66b is a controller for the lens unit 66a. In a measurement carried out by the subjective refractive power measurement apparatus 66, a test chart is presented through the corrective optical system provided at the test window. A refractive power of the eye E will be subjectively measured based on responses from the examinee.

Operations of the apparatus having above-described configuration will be explained hereinafter. First, the eye E is to be fixed at a predetermined position with use of the face support unit 2. As observing an image of the anterior part of the eye E displayed on the TV monitor 7, alignments are made by operating the joystick 5 and the rotation knob 5a so as to bring a reticle mark generated in the display circuit 51 and an image of the target for alignment formed by the target projecting optical system 40 into predetermined positions in relation to each other. When the alignment is completed, measurement is to be started at a push of the measurement starting switch 6.

The measurement light emitted from the light sources 11 successively passes through the condenser lens 12, the target plate 13, the beam splitter 42, the projecting lens 14 and the beam splitter 15, then converges in the vicinity of the cornea of the eye E. Thereafter, the measurement light arrives upon the fundus of the eye E thereby projects a target for measurement by the target plate 13 thereon. In case of an emmetropic eye, an image of the target for measurement reflected from the fundus of the eye E is reflected by the beam splitter 15, passes though the object lens 17, reflected again by the beam splitter 16, passes through the relay lense 18, the relay lense 19 and then the image forming lens 22 thereby form an image on the photo-detector 23. If the eye E has a refractive error, the motor 58 is driven so as to move the target plate 13 along with the movable lens 21 to a conjugate position with the fundus of the eye E in accordance with a receive signal responsive to reflected light from the fundus received by the photo-detector 23.

Next, the first relay lens 32 is moved so as to place the fixation target 34 and the fundus of the eye E at conjugate positions with each other, and further moves the first relay lens 32 so that the adequate amount of diopter is to be fogged. With the eye E being fogged, the light sources 11, the corneal reflection eliminating mask 20 and the photo-detector 23 are made to be rotated 180° about the optical axis. During the rotation, the target plate 13 and the movable lens 21 move in response to the signal from the photo-detector 23. The potentiometer 60 detects the amount of the movement and thereby obtains a value of a refractive power in each meridian direction. The controller 50 gives a predetermined process to the obtained refractive power so as to obtain values of S (spherical power), C (cylindrical power) and A (cylindrical axial angle). For this measurement method of an eye refractive power, see U.S. Pat. No. 5,500,697 corresponding to Japanese Patent Publication of unexamined patent application No. HEI 7-39517 by the present applicant.

Such measurement as described above is repeated a plurality of times on one and the same eye to be examined. The measurement may be repeated by depressing the measurement starting switch 6 a plurality of times or by programming to do so automatically in response to one trigger signal (measurement starting signal). The controller 50 stores the data obtained from the repeated measurements into the memory 62 and gives a predetermined statistical process to the data so as to obtain its typical value. This is to select an initial corrective optical system in accordance with the typical value for a subjective refractive power measurement which is to be performed next, which allows even an unskilled examiner in optometry to easily decide an accurate initial value for the corrective optical system. The typical value may be decided, for example, by ranking the obtained values in order of their sizes to make the median be the typical value (or the average value of all the obtained data can be the typical value).

As well as calculating the typical value, the controller 50 judges whether or not the eye possibly has low hyperopia. In cases where it is judged that the eye possibly has low hyperopia, the controller 50 calculates a desirable value (hereinafter mentioned as a recommendation value) which is a suitable value to be used as an initial value in the subjective refractive power measurement.

It is judged that the eye possibly has low hyperopia in cases where (a) both positive and negative spherical powers are included in the obtained values of S, (b) all the values of S are equal to 0D [Diopter], both 0D and negative spherical powers are included in the obtained values of S, or all the values of S are negative spherical powers and weaker than a predetermined standard value (for example, −1.00 D or greater). When it is judged that the eye possibly has low hyperopia, the recommendation value is decided in the following way.

In the cases of (a), the greatest value of S among all the measurement data is picked out to be the recommendation value. It is also possible to determine the recommendation value by adding a predetermined value to the average or the median of the obtained data from which data of S having negative degrees is excluded.

In the case of (b), to obtain the recommendation value, a predetermined positive value (for example, +1.00 D) is added to the typical value of S which is calculated in the aforementioned statistical process.

In the cases of (a) and (b) as described above, if it is programmed that the examiner can arbitrarily set the values such as the standard value to judge whether or not the eye possibly has low hyperopia, the positive value to be added to the value of S and the value to be added to the average or the median by operating the switch part 8, the values can be set in agreement with his policy, which will be suitable for a subjective measurement to be performed next.

The typical value obtained in the aforementioned way as well as the recommendation value obtained in the case of the eye which possibly has low hyperopia will be printed out from the printer 63 together with other measurement results with a push of a print switch in the switch part 8. If the recommendation value is included in the printout, the examiner will easily notice that the eye may have low hyperopia. By selecting an initial corrective optical system in the subjective refractive power measurement based on the recommendation value, the examiner can appropriately obtain the corrective value for hyperopic eye even in the case where the eye actually has low hyperopia.

In the case where the subjective refractive power measurement apparatus 66 is connected to the apparatus of the preferred embodiment, the recommendation value will be sent to a controller 66b via the interface circuit 65 with a push of the print switch. When it is judged that the eye possibly has low hyperopia, the recommendation value will take priority in transmission. The subjective eye refractive power measurement device 66 will select the initial corrective optical system to be arranged at the test window of the lens unit 66a in accordance with the typical value or the recommendation value.

In the embodiment described above, when it is judged that the eye possibly has low hyperopia, the recommendation value is to be printed out along with the typical value. However, in the case of (a) mentioned above, it is also possible to program so as to print out only the recommendation value and use the recommendation value as the typical value on account of the fact that the possibility of the eye having low hyperopia is relatively high.

Figure 4:
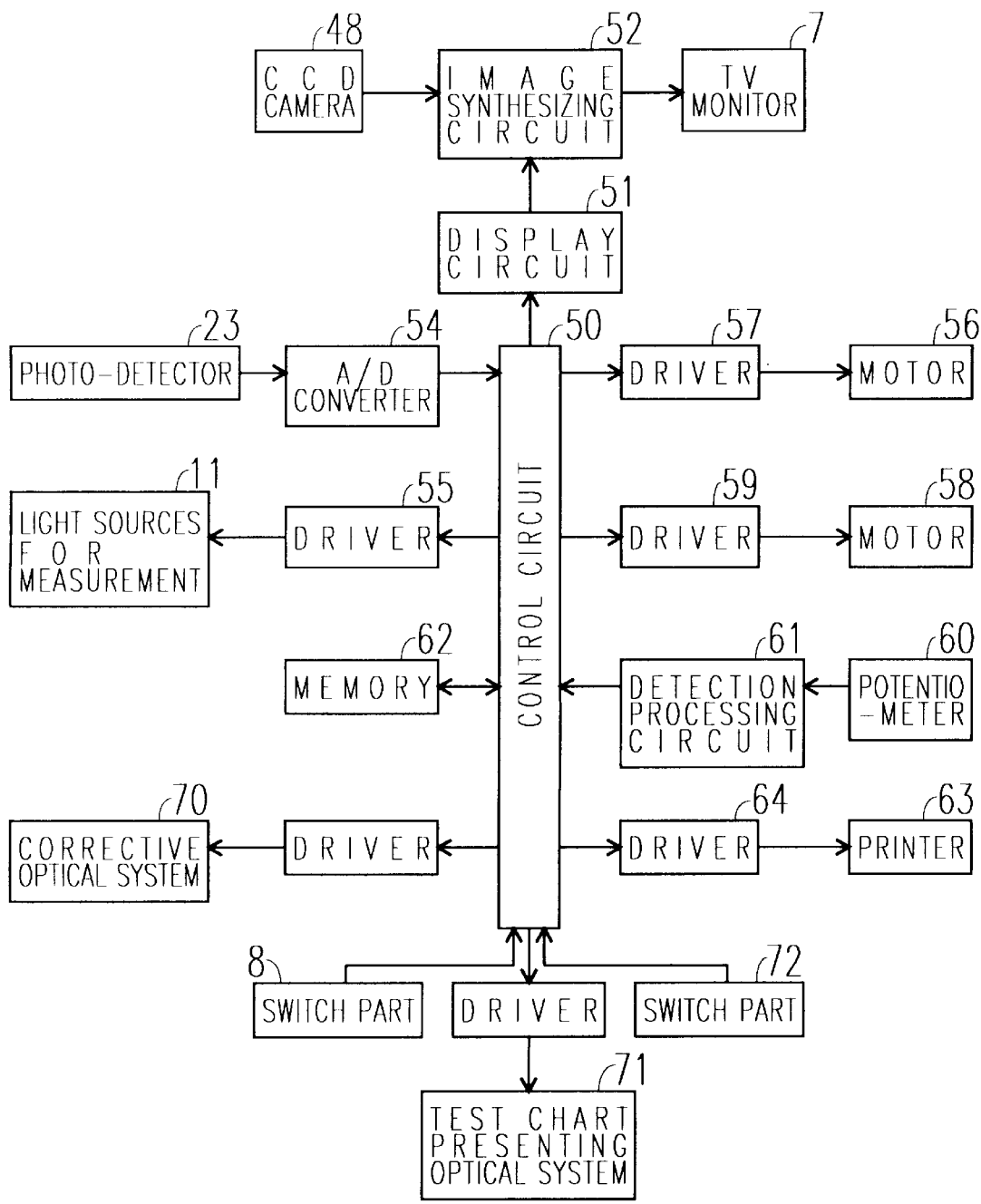
FIG. 4 is a view showing a schematic arrangement of a control system of the apparatus according to the modified embodiment of the present invention.

In addition, in stead of the apparatus in the embodiment which consists of only objective measurement means, the apparatus may be combined with a corrective optical system 70 to subjectively measures a refractive power of the eye, a test chart presenting optical system 71 and the like (see FIG. 4). In the case of this arrangement, the initial value of the corrective optical system 70 will be selected automatically based on the typical value or the recommendation value mentioned above. Reference numeral 72 in FIG. 4 denotes a switch part to be utilized when the examiner switches the corrective optical system 70, the test chart presenting optical system 71, and the like.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus including measurement means for objectively measuring a refractive power of an eye to be examined, the apparatus comprising:

memory means for storing a plurality of measurement results obtained by said measurement means;

typical value determination means for determining a typical value of the measurement results based on the plurality of the measurement results stored in said memory means;

judging means for judging whether or not the eye possibly has low hyperopia based on the plurality of the measurement results stored in said memory means;

recommendation value determination means for determining a recommendation value which is different from said typical value if said judging means judges that the eye possibly has low hyperopia; and data output means for outputting data indicating said typical value and/or said recommendation value.

2. The eye refractive power measurement apparatus according to claim 1, wherein said judging means judges that the eye possibly has low hyperopia if data indicating low myopia or hyperopia is included in the plurality of the measurement results stored in said memory means.

3. The eye refractive power measurement apparatus according to claim 1, wherein said judging means judges that the eye possibly has low hyperopia if: both positive and negative spherical powers are included in the plurality of the measurement results stored in said memory means, all of said measurement results substantially equal 0 diopter spherical power, all of said measurement results are either 0 diopter spherical power or negative spherical power, all of said measurement results are negative spherical powers and are greater than a predetermined negative spherical power.

4. The eye refractive power measurement apparatus according to claim 3, further comprising changing means with which the examiner can arbitrarily change said predetermined negative spherical power.

5. The eye refractive power measurement apparatus according to claim 1, wherein said recommendation value determination means determines the recommendation value by selecting a greatest spherical power among said measurement results or by giving a predetermined process to said measurement results from which data indicating a negative spherical power is excluded if both positive and negative spherical powers are included in said plurality of the measurement results whereby said judging means judges that the eye possibly has low hyperopia, or by adding a predetermined value to said typical value if: all of said measurement results substantially equal 0 diopter spherical power, all of said measurement results are either 0 diopter spherical power or negative spherical power, or all of said measurement results are negative spherical powers and are greater than a predetermined negative spherical power, whereby said judging means judges that the eye possibly has low hyperopia.

6. The eye refractive power measurement apparatus according to claim 5, wherein said recommendation value determination means comprising:

recommendation value calculating means for calculating the recommendation value by adding the predetermined value to a median or an average of said measurement results from which data indicating a negative spherical power is excluded; and changing means with which the examiner can arbitrarily change the predetermined value to be added to said median or said average.

7. The eye refractive power measurement apparatus according to claim 5, wherein said recommendation value determination means comprising:

recommendation value calculating means for calculating the recommendation value by adding the predetermined value to said typical value; and changing means with which the examiner can arbitrarily change the predetermined value to be added to said typical value.

8. The eye refractive power measurement apparatus according to claim 1, wherein said typical value determination means comprising:

extracting means for extracting a median of the plurality of the measurement results stored in said memory means; and/or average calculating means for calculating an average of the plurality of the measurement results stored in said memory means.

9. The eye refractive power measurement apparatus according to claim 1, wherein said typical value or said recommendation value output by said data output means is utilized as data for setting an initial value for a corrective optical system in subjective refractive power measurement.

10. The eye refractive power measurement apparatus according to claim 1, wherein said data output means outputs both said typical value and said recommendation value if it is judged that the eye possibly has low hyperopia.

11. The eye refractive power measurement apparatus according to claim 1, wherein said data output means outputs only said recommendation value if both positive and negative spherical powers are included in said plurality of the measurement results whereby said judging means judges that the eye possibly has low hyperopia.

12. The eye refractive power measurement apparatus according to claim 1, further comprising:

transmitting means for transmitting data indicating said typical value and/or said recommendation value output by said data output means to an eye refractive power measurement apparatus for subjectively measuring the refractive power of the eye.

13. The eye refractive power measurement apparatus according to claim 1, further comprising:

output control means for controlling output by said data output means so as to outputs only said recommendation value if said judging means judges that the eye possibly has low hyperopia; and transmitting means for transmitting data indicating said recommendation value output by said data output means to an eye refractive power measurement apparatus for subjectively measuring the refractive power of the eye.

14. An eye refractive power measurement apparatus including measurement means for objectively measuring a refractive power of an eye to be examined, the apparatus comprising:

memory means for storing a plurality of measurement results obtained by said measurement means;

typical value determination means for determining a typical value of the measurement results by giving a predetermined statistical process to the plurality of the measurement results stored in said memory means;

judging means for judging that the eye possibly has low hyperopia if, both positive and negative spherical powers are included in the plurality of the measurement results stored in said memory means, all of said measurement results substantially equal 0 diopter spherical power, all of said measurement results are either 0 diopter spherical power or negative spherical power, or all of said measurement results are negative spherical powers and are greater than a predetermined negative spherical power;

recommendation value determination means for determining a recommendation value which is different from said typical value by giving a predetermined process if said judging means judges that the eye possibly has low hyperopia; and data output means for outputting data indicating said typical value and/or said recommendation value.

15. The eye refractive power measurement apparatus according to claim 14, wherein said typical value determination means obtains a median or an average of the plurality of the measurement results stored in said memory means so as to determine said typical value by selecting said median or said average.

16. The eye refractive power measurement apparatus according to claim 14, wherein said recommendation value determination means determines the recommendation value by selecting a greatest spherical power among said measurement results if both positive and negative spherical powers are included in said plurality of the measurement results, or by adding a predetermined value to said typical value if, all of said measurement results substantially equal 0 diopter spherical power, all of said measurement results are either 0 diopter spherical power or negative spherical power, or all of said measurement results are negative spherical powers and are greater than a predetermined negative spherical power.

17. An eye refractive power measurement apparatus for measuring a refractive power of an eye to be examined, the apparatus comprising:

objective measurement means for objectively measuring the refractive power of the eye;

memory means for storing a plurality of measurement results obtained by said objective measurement means;

typical value determination means for determining a typical value of the measurement results based on the plurality of the measurement results stored in said memory means;

judging means for judging whether or not the eye possibly has low hyperopia based on the plurality of the measurement results stored in said memory means;

recommendation value determination means for determining a recommendation value which is different from said typical value if said judging means judges that the eye possibly has low hyperopia;

subjective measurement means for subjectively measuring the refractive power of the eye; and subjective measurement control means for controlling said subjective measurement means based on data indicating said typical value and/or said recommendation value.

18. The eye refractive power measurement apparatus according to claim 17, wherein said objective measurement means comprising:

a projecting optical system for projecting a target for measurement onto a fundus of the eye;

a detection optical system for detecting an image of the target projected by said projecting optical system; and refractive power calculating means for calculating the refractive power of the eye based on results detected by said detection optical system.

19. The eye refractive power measurement apparatus according to claim 17, wherein said subjective measurement means comprising:

test chart presenting means for presenting a test chart onto the eye;

a corrective optical system which is arranged in front of the eye;

driving means for driving said corrective optical system; and wherein said subjective measurement control means controls said driving means so as to set an initial value for said corrective optical system based on data indicating said typical value and/or said recommendation value.

20. The eye refractive power measurement apparatus according to claim 17, wherein said subjective measurement control means controls said subjective measurement means based on data indicating said recommendation value if said judging means judges that the eye possibly has low hyperopia.

* * * * *